United States Patent
McCormack et al.

[11] Patent Number: 6,111,163
[45] Date of Patent: *Aug. 29, 2000

[54] ELASTOMERIC FILM AND METHOD FOR MAKING THE SAME

[75] Inventors: Ann L. McCormack, Cumming; William B. Haffner, Kennesaw, both of Ga.

[73] Assignee: Kimberly-Clark Worldwide, Inc., Neenah, Wis.

[ * ] Notice: This patent issued on a continued prosecution application filed under 37 CFR 1.53(d), and is subject to the twenty year patent term provisions of 35 U.S.C. 154(a)(2).

[21] Appl. No.: 08/883,164

[22] Filed: Jun. 26, 1997

Related U.S. Application Data

[63] Continuation of application No. 08/775,067, Dec. 27, 1996, abandoned.

[51] Int. Cl.[7] ............................. A61F 13/15; C08J 3/00; B29C 65/00
[52] U.S. Cl. ......................... 604/367; 264/41; 264/453; 524/426
[58] Field of Search .......................... 264/41, 154, 45.3; 524/426; 604/358, 367, 389

[56] References Cited

U.S. PATENT DOCUMENTS 1,741,530  12/1929  Mayer .
2,971,322   2/1961  Bouvet .

(List continued on next page.)

FOREIGN PATENT DOCUMENTS

| 0 030 418 | 6/1981 | European Pat. Off. . |
| 0 105 629 B1 | 4/1984 | European Pat. Off. . |
| 0 127 483 A2 | 12/1984 | European Pat. Off. . |
| 0 194 150 A2 | 9/1986 | European Pat. Off. . |
| 0 214 859 A2 | 3/1987 | European Pat. Off. . |
| 0 227 481 | 7/1987 | European Pat. Off. . |
| 0 180 703 | 3/1989 | European Pat. Off. . |

(List continued on next page.)

OTHER PUBLICATIONS

HPT Plastics Update (Nov., 1995), "Metallocene Resins Promise Revolution in Films," p. 1, col. 3.
Abstract for European Document No. 0 019 295.
Abstract for European Document No. 0 237 642.
Abstract for European Document No. 2205407.

(List continued on next page.)

*Primary Examiner*—Robert A. Clarke
*Assistant Examiner*—Dennis Ruhl

[57] ABSTRACT

The present invention relates to a breathable, oriented microporous elastomeric film. The present invention also relates to a process for forming the breathable film including the step of stretching a filled film to produce a microporous film layer.

18 Claims, 2 Drawing Sheets

U.S. PATENT DOCUMENTS

| | | |
|---|---|---|
| 3,047,444 | 7/1962 | Harwood . |
| 3,059,313 | 10/1962 | Harmon . |
| 3,256,258 | 6/1966 | Herrman . |
| 3,338,992 | 8/1967 | Kinney . |
| 3,341,394 | 9/1967 | Kinney . |
| 3,396,071 | 8/1968 | Couzens . |
| 3,406,033 | 10/1968 | Reitz . |
| 3,438,844 | 4/1969 | Kumin . |
| 3,485,695 | 12/1969 | Ness . |
| 3,502,538 | 3/1970 | Petersen . |
| 3,542,615 | 11/1970 | Dobo et al. . |
| 3,575,784 | 4/1971 | Phillips et al. . |
| 3,679,538 | 7/1972 | Druin et al. . |
| 3,692,618 | 9/1972 | Dorschner et al. . |
| 3,772,417 | 11/1973 | Vogt . |
| 3,802,817 | 4/1974 | Matsuki et al. . |
| 3,843,761 | 10/1974 | Bierenbaum et al. . |
| 3,880,966 | 4/1975 | Zimmerman et al. . |
| 3,932,682 | 1/1976 | Loft et al. . |
| 3,949,128 | 4/1976 | Ostermeier . |
| 4,013,816 | 3/1977 | Sabee et al. . |
| 4,041,203 | 8/1977 | Brock et al. . |
| 4,047,534 | 9/1977 | Thormaschefsky et al. . |
| 4,125,114 | 11/1978 | Repke . |
| 4,147,827 | 4/1979 | Breidt, Jr. et al. . |
| 4,166,464 | 9/1979 | Korpman ............................. 128/287 |
| 4,187,210 | 2/1980 | Howard, Jr. . |
| 4,193,899 | 3/1980 | Brenner et al. . |
| 4,197,150 | 4/1980 | Breidt, Jr. et al. . |
| 4,209,563 | 6/1980 | Sisson . |
| 4,303,571 | 12/1981 | Jansen et al. . |
| 4,303,708 | 12/1981 | Gebhardt et al. . |
| 4,323,534 | 4/1982 | DesMarais . |
| 4,333,979 | 6/1982 | Sciaraffa et al. . |
| 4,340,563 | 7/1982 | Appel et al. . |
| 4,342,812 | 8/1982 | Selwood . |
| 4,347,844 | 9/1982 | Ohki et al. . |
| 4,350,655 | 9/1982 | Hoge . |
| 4,364,985 | 12/1982 | Tokuyama et al. . |
| 4,384,024 | 5/1983 | Mitchell et al. . |
| 4,418,123 | 11/1983 | Bunnelle et al. . |
| 4,434,258 | 2/1984 | Schumacher et al. . |
| 4,436,780 | 3/1984 | Hotchkiss et al. . |
| 4,443,511 | 4/1984 | Worden et al. . |
| 4,443,513 | 4/1984 | Meitner et al. . |
| 4,467,595 | 8/1984 | Kramers . |
| 4,472,328 | 9/1984 | Sugimoto et al. . |
| 4,486,485 | 12/1984 | Sookne . |
| 4,489,543 | 12/1984 | Bromley et al. . |
| 4,515,854 | 5/1985 | Kogame et al. . |
| 4,533,602 | 8/1985 | Nakamura et al. . |
| 4,551,378 | 11/1985 | Carey, Jr. . |
| 4,552,709 | 11/1985 | Koger, II et al. . |
| 4,554,121 | 11/1985 | Kramers . |
| 4,554,207 | 11/1985 | Lee . |
| 4,578,307 | 3/1986 | Niki et al. . |
| 4,585,604 | 4/1986 | Okuyama et al. . |
| 4,606,964 | 8/1986 | Wideman . |
| 4,606,970 | 8/1986 | Sharps, Jr. . |
| 4,609,584 | 9/1986 | Cutler et al. . |
| 4,612,148 | 9/1986 | Motooka et al. . |
| 4,613,643 | 9/1986 | Nakamura et al. . |
| 4,652,487 | 3/1987 | Morman . |
| 4,657,802 | 4/1987 | Morman . |
| 4,668,566 | 5/1987 | Braun . |
| 4,696,779 | 9/1987 | Wideman . |
| 4,698,372 | 10/1987 | Moss . |
| 4,704,238 | 11/1987 | Okuyama et al. . |
| 4,705,812 | 11/1987 | Ito et al. . |
| 4,720,415 | 1/1988 | Vander Wielen et al. . |
| 4,725,473 | 2/1988 | Van Gompel et al. . |
| 4,734,324 | 3/1988 | Hill . |
| 4,753,834 | 6/1988 | Braun et al. . |
| 4,761,324 | 8/1988 | Rautenberg et al. . |
| 4,767,580 | 8/1988 | Shingo et al. . |
| 4,777,073 | 10/1988 | Sheth . |
| 4,793,956 | 12/1988 | Nogiwa et al. . |
| 4,794,128 | 12/1988 | Kawaguchi et al. . |
| 4,801,494 | 1/1989 | Datta et al. . |
| 4,806,300 | 2/1989 | Walton et al. . |
| 4,814,124 | 3/1989 | Aoyama et al. . |
| 4,822,350 | 4/1989 | Ito et al. . |
| 4,824,718 | 4/1989 | Hwang . |
| 4,829,096 | 5/1989 | Kitamura et al. . |
| 4,847,134 | 7/1989 | Fahrenkrug et al. . |
| 4,863,779 | 9/1989 | Daponte . |
| 4,868,222 | 9/1989 | Chau et al. . |
| 4,879,078 | 11/1989 | Antoon, Jr. . |
| 4,902,553 | 2/1990 | Hwang et al. . |
| 4,906,513 | 3/1990 | Kebbell et al. . |
| 4,919,738 | 4/1990 | Ball et al. . |
| 4,921,653 | 5/1990 | Aoyama et al. . |
| 4,923,650 | 5/1990 | Antoon, Jr. et al. . |
| 4,923,703 | 5/1990 | Antoon, Jr. . |
| 4,929,303 | 5/1990 | Sheth . |
| 4,952,451 | 8/1990 | Mueller . |
| 4,981,747 | 1/1991 | Morman . |
| 5,026,591 | 6/1991 | Henn et al. . |
| 5,110,677 | 5/1992 | Barmore et al. . |
| 5,140,073 | 8/1992 | Rolando et al. . |
| 5,143,679 | 9/1992 | Weber et al. . |
| 5,169,706 | 12/1992 | Collier, IV et al. . |
| 5,169,712 | 12/1992 | Tapp . |
| 5,173,235 | 12/1992 | Kamei et al. . |
| 5,176,953 | 1/1993 | Jacoby et al. . |
| 5,188,885 | 2/1993 | Timmons et al. . |
| 5,208,098 | 5/1993 | Stover . |
| 5,209,984 | 5/1993 | Rolando et al. . |
| 5,229,191 | 7/1993 | Austin . |
| 5,238,618 | 8/1993 | Kinzer . |
| 5,238,623 | 8/1993 | Mrozonski . |
| 5,238,636 | 8/1993 | Furukawa et al. . |
| 5,244,482 | 9/1993 | Hassenboehler, Jr. et al. . |
| 5,258,419 | 11/1993 | Rolando et al. . |
| 5,260,360 | 11/1993 | Mrozinski et al. . |
| 5,264,219 | 11/1993 | Godbey et al. . |
| 5,266,394 | 11/1993 | Diehl et al. . |
| 5,272,236 | 12/1993 | Lai et al. . |
| 5,273,596 | 12/1993 | Newkirk . |
| 5,296,291 | 3/1994 | Mueller . |
| 5,332,613 | 7/1994 | Taylor et al. . |
| 5,334,446 | 8/1994 | Quantrille et al. . |
| 5,336,545 | 8/1994 | Morman . |
| 5,366,786 | 11/1994 | Connor et al. . |
| 5,372,819 | 12/1994 | Godbey et al. . |
| 5,382,400 | 1/1995 | Pike et al. . |
| 5,393,599 | 2/1995 | Quantrille et al. . |
| 5,409,761 | 4/1995 | Langley . |
| 5,415,925 | 5/1995 | Austin et al. . |
| 5,425,987 | 6/1995 | Shawver et al. . |
| 5,431,643 | 7/1995 | Ouellette et al. . |
| 5,437,653 | 8/1995 | Gilman et al. . |
| 5,445,862 | 8/1995 | Kaneko et al. . |
| 5,445,874 | 8/1995 | Shehata . |
| 5,467,765 | 11/1995 | Maturaporn . |
| 5,470,639 | 11/1995 | Gessner et al. . |
| 5,470,640 | 11/1995 | Modrak . |
| 5,472,775 | 12/1995 | Obijeski et al. . |
| 5,482,765 | 1/1996 | Bradley et al. . |
| 5,484,645 | 1/1996 | Lickfield et al. . |
| 5,491,016 | 2/1996 | Kaiser et al. . |
| 5,492,751 | 2/1996 | Butt, Sr. et al. . |

| | | |
|---|---|---|
| 5,494,680 | 2/1996 | Peterson . |
| 5,498,463 | 3/1996 | McDowall et al. . |
| 5,518,801 | 5/1996 | Chappell et al. . |
| 5,522,810 | 6/1996 | Allen, Jr. et al. .......... 604/366 |
| 5,529,845 | 6/1996 | Branchesi et al. . |
| 5,536,555 | 7/1996 | Zelazoski et al. . |
| 5,540,976 | 7/1996 | Shawver et al. . |
| 5,543,206 | 8/1996 | Austin et al. . |
| 5,580,411 | 12/1996 | Nease et al. . |
| 5,592,690 | 1/1997 | Wu . |
| 5,681,627 | 10/1997 | Mueller . |
| 5,683,533 | 11/1997 | Keighley et al. .......... 604/389 |
| 5,786,058 | 7/1998 | Megchelsen et al. . |
| 5,789,065 | 8/1998 | Haffner et al. . |
| 5,804,519 | 9/1998 | Riswick et al. . |
| 5,865,919 | 2/1999 | Megchelsen et al. . |

FOREIGN PATENT DOCUMENTS

| | | |
|---|---|---|
| 0 311 423 | 4/1989 | European Pat. Off. . |
| 0 444 671 A3 | 9/1991 | European Pat. Off. . |
| 0 505 027 B1 | 9/1992 | European Pat. Off. . |
| 0 549 954 A1 | 7/1993 | European Pat. Off. . |
| 0 554 896 A1 | 8/1993 | European Pat. Off. . |
| 0 605 831 A1 | 7/1994 | European Pat. Off. . |
| 0 659 808 A1 | 6/1995 | European Pat. Off. . |
| 0 693 585 A2 | 1/1996 | European Pat. Off. . |
| 0 779 325 A2 | 6/1997 | European Pat. Off. . |
| 2205407 | 11/1972 | France . |
| 2046593 | 11/1971 | Germany . |
| 1460514 | 3/1977 | Germany . |
| 2757526 | 6/1979 | Germany . |
| 2632875 | 1/1982 | Germany . |
| 3438859 | 7/1985 | Germany . |
| 2613963 | 1/1986 | Germany . |
| 3724510 | 2/1989 | Germany . |
| 4-227260 | 8/1992 | Japan . |
| 8-048804 | 2/1996 | Japan . |
| 8-053561 | 2/1996 | Japan . |
| 1217498 | 12/1970 | United Kingdom . |
| 1308904 | 3/1973 | United Kingdom . |
| 1399666 | 7/1975 | United Kingdom . |
| 1 532 467 | 11/1978 | United Kingdom . |
| 2 027 637 | 2/1980 | United Kingdom . |
| 1 576 436 | 10/1980 | United Kingdom . |
| 1575972 | 10/1980 | United Kingdom . |
| 2 149 720 | 6/1985 | United Kingdom . |
| 2175026 | 11/1986 | United Kingdom . |
| WO 94/04606 | 3/1994 | WIPO . |
| WO 95/16562 | 6/1995 | WIPO . |
| WO 96/19346 | 6/1996 | WIPO . |
| 97/04955 | 2/1997 | WIPO . |

OTHER PUBLICATIONS

Abstract for Germany Document No. 1460514.

Abstract for Germany Document No. 2046593.

Abstract for Germany Document No. 2613963.

Abstract for Germany Document No. 2632875.

Abstract for Germany Document No. 2757526.

Abstract for Germany Document No. 3438859.

Abstract for Germany Document No. 3724510.

Excerpt from *Modern Plastics International*, Oct. 1992, "Dow says octene LLDPEs improve blown and cast film properties".

Naitove, Matthew H., "High–performance PEs for packaging." *Plastics Technology*, v38, n11, p21(3).

"Kangaroo Brands Jumps at an Opportunity", *Packag. Dig.*, v30, no. 4, Apr. 1993, pp. 42,44,46.

Leaversuch, Robert D., "LLDPE resin advances promise new growth in tough film.", *Modern Plastics*, v72, n6, p42(4), Jun. 1995.

"New linear low–density polyethylene resin technologies guarantee introduction of newer and better films", *Modern Plastics International*, Jun., 1995, p.38.

Keith Kreisher, "Navigating the Materials malestrom", *Modern Plastics*, May, 1995, p. 47, v72, n5.

"New generation DOWLEX Family of resins debuts from Dow Plastics.", *Food Engineering*, v64, n12, p50(2), Oct., 1992.

Abstract: "Octene LLDPE grade aimed at the stretch film market.", *Modern Plastics*, v22, n10, Oct., 1992, p151.

Leaversuch, R.D., Supertough PE Films Aid Downgauging Drive, *Modern Plastics*, v24, n8, p55(9), Aug., 1994.

Leaversuch, R.D., "'Supertough' PE Films Aid Downgauging of Packaging", *Modern Plastics*, v71, n8, p19, Aug., 1994.

"Tough metallocene LLDPE enters the big time", *Canadian Plastics*, p19, Apr., 1996.

FIG. 1

ELASTOMERIC FILM AND METHOD FOR MAKING THE SAME

CROSS-REFERENCE TO RELATED APPLICATION

This application is a continuation of application Ser. No. 08/775,067 filed on Dec. 27, 1996, abandoned the contents of which are incorporated herein by reference.

FIELD OF INVENTION

The present invention is directed to laminates of at least one filled elastomeric film and at least one support layer such as a fibrous nonwoven web. In addition, the present invention is directed to a method of making such laminates.

BACKGROUND OF THE INVENTION

The present invention is directed to breathable elastomeric films and laminates thereof. Such materials have a wide variety of uses, especially in the areas of limited use and disposable items.

Films have been traditionally used to provide barrier properties in limited use or disposable items. By limited use or disposable, it is meant that the product and/or component is used only a small number of times or possibly only once before being discarded. Examples of such products include, but are not limited to, surgical and health care related products such as surgical drapes and gowns, disposable work wear such as coveralls and lab coats and personal care absorbent products such as diapers, training pants, incontinence garments, sanitary napkins, bandages, wipes and the like. In personal care absorbent products such as infant diapers and adult incontinence products, films are used as the outer covers with the purpose of preventing body wastes from contaminating the clothing, bedding and other items in the surrounding environment of use. In the area of protective apparel including hospital gowns, films are used to prevent cross exchange of microorganisms between the wearer and the patient.

While these films can be effective barriers, they are not aesthetically pleasing because their surfaces are smooth and either feel slick or tacky. They are also visually flat and "plasticy" thereby making them less desirable in apparel applications and other uses where they are in contact with human skin. It would be more preferable if these items were more cloth-like from both a tactile and visual standpoint. For example, infant diapers that have the feel and appearance of traditional cloth undergarments are perceived as premium products and may, in some cases, overcome the tendency to believe that they need to be covered by outer garments for aesthetic reasons. Garment-like adult incontinence products could improve the self-image of the incontinent individual. In addition, more garment-like isolation gowns would help the hospital environment feel less foreign and threatening to the patient and increase the comfort of the wearer. It is also preferable to have films that can make an outercover material with more elastic give and recovery to provide better fit and comfort.

Lamination of films have been used to create materials which are both impervious and somewhat cloth-like in appearance and texture. The outer covers on disposable diapers are but one example. In this regard, reference may be had to coassigned U.S. Pat. No. 4,818,600 dated Apr. 4, 1989 and U.S. Pat. No. 4,725,473 dated Feb. 16, 1988. Surgical gowns and drapes are other examples. See, in this regard, coassigned U.S. Pat. No. 4,379,102 dated Apr. 5, 1983.

A primary purpose of the film in such laminations is to provide barrier properties. There is also a need for such laminates to be breathable so that they have the ability to transmit moisture vapor. Apparel made from laminations of these breathable or microporous films are more comfortable to wear by reducing the moisture vapor concentration and the consequent skin hydration underneath the apparel item.

There is therefore a need for an elastic breathable film and process that provides a film with both the cloth-like aesthetics and the fit and comfort that are desired.

SUMMARY OF THE INVENTION

The present invention relates to a breathable laminate including at least one support layer and an oriented microporous film that includes an elastomeric resin and at least 30% by weight of the film of a filler having a particle size that contributes to pore formation.

In one embodiment of the present invention, the elastomeric resin includes a polymeric material selected from block copolymers including styrene, copolymers of ethylene and propylene, terpolymers including ethylene and propylene, Catalloy® brand resins, ethylene vinyl acetates, ethylene-normal butyl acrylates, ethylene methyl acrylates, Polytrope® brand ethylene-propylene elastomer blends and metallocene catalyzed ethylene based polymers.

The present invention also is directed to a process for producing a laminate including at least one support layer and an oriented microporous elastomeric film including the steps of providing a filled film layer having a first length that includes at least 30% by weight of a filler having a particle size that contributes to pore formation and an elastic polymeric material that is capable of being stretched at room temperature to at least twice its original length and, upon release of the stretching force, will retract approximately to its original unstretched length; stretching the filled film to produce a microporous film having a second length; and bonding at least one support layer to the microporous film to form a laminate.

The film of the present invention has a water vapor transmission rate of from at least about 300 $g/m^2$-24 hrs, preferably about 1,000 to about 4,500 $g/m^2$-24 hrs. or even higher (measured by ASTM Test E 96-80 with Celgard® 2500 as control).

Such films and laminates thereof have a wide variety of uses including, but not limited to, applications in personal care absorbent articles including diapers, training pants, sanitary napkins, incontinence devices, bandages and the like. These same films and laminates also may be used in items such as surgical drapes and gowns as well as various articles of clothing either as the entire article or simply as a component thereof.

DETAILED DESCRIPTION OF THE PREFERRED EMBODIMENTS

The present invention is directed to filled microporous oriented elastomeric films and laminates thereof.

The film of the present invention is an oriented microporous film that includes an elastomeric resin and at least 30% by weight of a filler having a particle size that contributes to pore formation.

Polymeric materials that are useful in the present invention are generally known as "elastomers," "synthetic rubbers" or "rubbers." Elastomers useful in the practice of this invention may be those made from block copolymers such as polyurethanes, copolyether esters, polyamide polyether block copolymers, ethylene vinyl acetates (EVA), block copolymers having the general formula A-B-A' or A-B like copoly(styrene/ethylene-butylene), styrene-poly(ethylene-propylene)-styrene, styrene-poly(ethylene-butylene)-styrene, (polystyrene/poly(ethylene-butylene)/polystyrene, poly(styrene/ethylene-butylene/styrene) and the like.

Useful elastomeric resins include block copolymers having the general formula A-B-A' or A-B, where A and A' are each a thermoplastic polymer endblock which contains a styrenic moiety such as a poly (vinyl arene) and where B is an elastomeric polymer midblock such as a conjugated diene or a lower alkene polymer. Block copolymers of the A-B-A' type can have different or the same thermoplastic block polymers for the A and A' blocks, and the present block copolymers are intended to embrace linear, branched and radial block copolymers. In this regard, the radial block copolymers may be designated (A-B)$_m$-X, wherein X is a polyfunctional atom or molecule and in which each (A-B)$_m$- radiates from X in a way that A is an endblock. In the radial block copolymer, X may be an organic or inorganic polyfunctional atom or molecule and m is an integer having the same value as the functional group originally present in X. It is usually at least 3, and is frequently 4 or 5, but not limited thereto. Thus, in the present invention, the expression "block copolymer", and particularly "A-B-A'" and "A-B" block copolymer, is intended to embrace all block copolymers having such rubbery blocks and thermoplastic blocks as discussed above, which can be extruded, without limitation as to the number of blocks.

Elastomeric polymers also include copolymers of ethylene and at least one vinyl monomer such as, for example, vinyl acetates, unsaturated aliphatic monocarboxylic acids, and esters of such monocarboxylic acids. The elastomeric copolymers and formation of elastomeric nonwoven webs from those elastomeric copolymers are disclosed in, for example, U.S. Pat. 4,803,117.

Ethylene copolymers useful in the present invention also include, for example, metallocene-catalyzed ethylene-based polymers. The term "metallocene-catalyzed ethylene-based polymers" as used herein includes those polymer materials that are produced by the polymerization of at least ethylene using metallocenes or constrained geometry catalysts, a class of organometallic complexes, as catalysts. For example, a common metallocene is ferrocene, a complex with a metal sandwiched between two cyclopentadienyl (Cp) ligands. Metallocene process catalysts include bis(n-butylcyclopentadienyl)titanium dichloride, bis(n-butylcyclopentadienyl)zirconium dichloride, bis(cyclopentadienyl)scandium chloride, bis(indenyl) zirconium dichloride, bis(methylcyclopentadienyl)titanium dichloride, bis(methylcyclopentadienyl)zirconium dichloride, cobaltocene, cyclopentadienyltitanium trichloride, ferrocene, hafnocene dichloride, isopropyl (cyclopentadienyl,-1-flourenyl)zirconium dichloride, molybdocene dichloride, nickelocene, niobocene dichloride, ruthenocene, titanocene dichloride, zirconocene chloride hydride, zirconocene dichloride, among others. A more exhaustive list of such compounds is included in U.S. Pat. No. 5,374,696 to Rosen et al. and assigned to the Dow Chemical Company. Such compounds are also discussed in U.S. Pat. No. 5,064,802 to Stevens et al. and also assigned to Dow.

The metallocene process, and particularly the catalysts and catalyst support systems are the subject of a number of patents. U.S. Pat. No. 4,542,199 to Kaminsky et al. describes a procedure wherein MAO is added to toluene, the metallocene catalyst of the general formula (cyclopentadienyl) 2MeRHal wherein Me is a transition metal, Hal is a halogen and R is cyclopentadienyl or a C1 to C6 alkyl radical or a halogen, is added, and ethylene is then added to form polyethylene. U.S. Pat. No. 5,189,192 to LaPointe et al. and assigned to Dow Chemical describes a process for preparing addition polymerization catalysts via metal center oxidation. U.S. Pat. No. 5,352,749 to Exxon Chemical Patents, Inc. describes a method for polymerizing monomers in fluidized beds. U.S. Pat. No. 5,349,100 describes chiral metallocene compounds and preparation thereof by creation of a chiral center by enantioselective hydride transfer.

Co-catalysts are materials such as methylaluminoxane (MAO) which is the most common, other alkylaluminums and boron containing compounds like tris (pentafluorophenyl)boron, lithium tetrakis (pentafluorophenyl)boron, and dimethylanilinium tetrakis (pentafluorophenyl)boron. Research is continuing on other co-catalyst systems or the possibility of minimizing or even eliminating the alkylaluminums because of handling and product contamination issues. The important point is that the metallocene catalyst be activated or ionized to a cationic form for reaction with the monomer(s) to be polymerized.

The metallocene-catalyzed ethylene-based polymers used in the present invention impart stretch and recovery properties to the film. Preferably, the metallocene catalyzed ethylene-based polymers selected from copolymers of ethylene and 1-butene, copolymers of ethylene and 1-hexene, copolymers of ethylene and 1-octene and combinations thereof. In particular, preferred materials include Affinity brand elastomeric metallocene-derived copolymers of ethylene and 1-octene, both available from Dow Plastics of Freeport, Tex. Particularly preferred materials also include Exact brand elastomer metallocene-derived copolymers and terpolymers of ethylene and 1-butene and copolymers of ethylene and 1-hexene, available from Exxon Chemical Company of Houston, Tex.

The thermoplastic copolyester elastomers include copolyetheresters having the general formula:

where "G" is selected from the group consisting of poly (oxyethylene)-alpha,omega-diol, poly(oxypropylene)-alpha, omega-diol, poly(oxytetramethylene)-alpha,omega-diol and "a" and "b" are positive integers including 2, 4 and 6, "m" and "n" are positive integers including 1–20. Such materials generally have an elongation at break of from about 600 percent to 750 percent when measured in accordance with ASTM D-638 and a melt point of from about 350° F. to about 400° F. (176 to 205° C.) when measured in accordance with ASTM D-2117.

In an embodiment of the present invention, the resin includes polymeric material selected from copolymers including polystyrene, ethylene copolymers, copolymers of ethylene and propylene, Catalloy® brand resin, ethylene vinyl acetate (preferably from about 18 to about 35 percent by weight acetate), ethylene-normal butyl acrylate (preferably from about 18 to about 30 percent by weight acrylate), and ethylene methyl acrylate (preferably from about 20 to about 30 percent by weight acrylate).

Block copolymers including styrene useful in the present invention also include styrene-isoprene-styrene materials having unsaturated isoprene in the polymer chain such as, for example, Vector® brand available from Dexco Polymers of Houston, Tex.

Terpolymers useful in the present invention include, for example, ethylene-propylene-diene terpolymers.

The Catalloy® brand resin is a resin including molecular blends of two or more polymers of propylene, or propylene with ethylene available from HIMONT Corporation of Wilmington, Del. The blending is achieved in the polymerization reactor by sequential, independent polymerization of monomers (the so-called "catalloy" process), so that the mixing is on the molecular level, the results of which are not generally achievable by polymeric blending (conventional compounding with pre-made resin). Suitable examples of Catalloy® brand resins include Catalloy® KS-057, KS-059, KS-075 and KS-085.

Polytrope®, available from A. Schulman Co., of Akron, Ohio, is a blend of an ethylene vinyl acetate copolymer with an ethylene propylene-diene monomer (EPDM) terpolymer.

In addition to the polymeric material, the film layer also includes a filler which enables development of micropores during orientation of the film. As used herein a "filler" is meant to include particulates and other forms of materials which can be added to the polymer and which will not chemically interfere with or adversely affect the extruded film but is able to be uniformly dispersed throughout the film. Generally, the fillers will be in particulate form and usually will have somewhat of a spherical shape with average particle sizes in the range of about 0.5 to about 8 microns preferably from about 0.5 to about 5 microns. The film of the present invention will usually contain at least 30 percent (%), preferably about 40 to about 70 percent, filler based upon the total weight of the film layer. More preferably, from about 45 to about 60 percent of filler is present in the film. Both organic and inorganic fillers are contemplated to be within the scope of the present invention provided that they do not interfere with the film formation process, the breathability of the resultant film or its ability to bond to another layer such as a fibrous polyolefin nonwoven web.

Examples of fillers include calcium carbonate ($CaCO_3$), various kinds of clay, silica ($SiO_2$), alumina, barium sulfate, sodium carbonate, talc, magnesium sulfate, titanium dioxide, zeolites, aluminum sulfate, cellulose-type powders, diatomaceous earth, magnesium sulfate, magnesium carbonate, barium carbonate, kaolin, mica, carbon, calcium oxide, magnesium oxide, aluminum hydroxide, pulp powder, wood powder, cellulose derivative, polymer particles, chitin and chitin derivatives. The filler particles may optionally be coated with a fatty acid, such as stearic acid, which may facilitate the free flow of the particles (in bulk) and their ease of dispersion into the polymer matrix.

It has been possible to create films with a water vapor transmission rate (WVTR) of at least 300 grams per square meters per 24 hours ($g/m^2$-24 hrs), preferably from about 1,000 to about 4,500 based upon ASTM Standard Test E 96-80 with Celgard® 2500 as control.

In addition, the preferred films of the present invention are also elastic. The term "elastic" is used herein to mean any material which, upon application of a biasing force, is stretchable, that is, elongatable, to a stretched, biased length which is at least about 150 percent of its relaxed unbiased length, and which will recover at least 50 percent of its elongation upon release of the stretching, elongating force. A hypothetical example would be a one (1) inch sample of a material which is elongatable to at least 1.50 inches and which, upon being elongated to 1.50 inches and released, will recover to a length of not more than 1.25 inches. Many elastic materials may be stretched by much more than 50 percent of their relaxed length, for example, 100 percent or more, and many of these will recover to substantially their original relaxed length, for example, to within 105 percent of their original relaxed length, upon release of the stretching force.

These properties can be obtained by first preparing an elastomeric resin, then filling the resin with filler, forming a film from the filled resin and thereafter stretching or orienting the film usually in the machine direction, as explained in greater detail below, such that the resultant film is microporous and has increased strength properties in the machine direction, i.e., the direction which is parallel to the direction of the film as it is taken off the film extrusion equipment.

Figure 1:
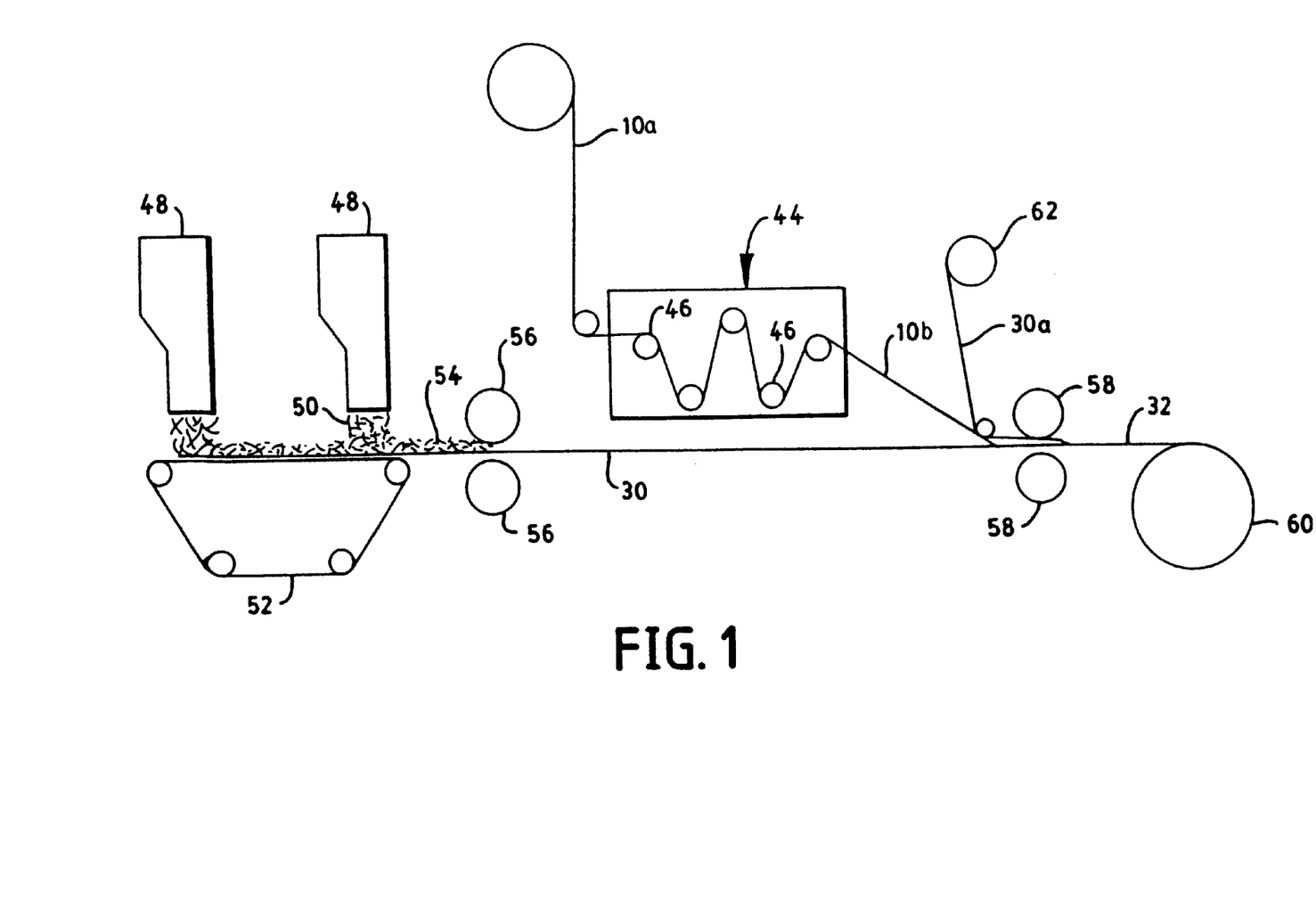
FIG. 1 is a schematic side view of a process for forming a film laminate according to the present invention.

Process for forming films and orienting these are well known to those skilled in the art. An example of film orienting and lamination process is shown in FIG. 1. Filled film 10a is directed to a film stretching unit 44 such as a machine direction orienter, which is a commercially available device from vendors such as the Marshall and Williams Company of Providence, R.I. Such an apparatus 44 has a plurality of stretching rollers 46 moving at progressively faster speeds relative to the pair disposed before it. These rollers 46 apply an amount of stress and thereby progressively stretch filled film 10a to a stretch length in the machine direction of the film which is the direction of travel of filled film 10a through the process as shown in FIG. 1. The stretch rollers 46 may be heated for better processing. In addition, unit 44 may also include rollers (not shown) upstream and/or downstream from the stretch rollers 46 that can be used to preheat the film 10a before orienting and/or anneal (or cool) it after stretching.

At the stretched length, a plurality of micropores form in the film. Preferably, the stretched length is from about two to about six, more preferably from about three to about four, times the original length of the film prior to stretching. Film 10b is then directed out of apparatus 44 so that the stress is removed to allow the stretched film to relax. Preferably, a permanent elongation length of at least about 1.5 more preferably about 3.0, times the original length is retained after the stretched film is allowed to relax. When the polymeric material is highly elastic, such as is the case with Vector® brand styrene-isoprene-styrene material, the more preferred stretch length is about five to about six times the original length, so that a desired permanent elongation is retained.

Figure 2:
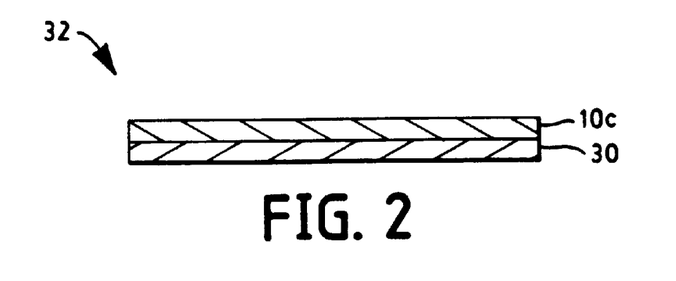
FIG. 2 is a cross-section side view of a film/nonwoven laminate according to the present invention.

Oftentimes it may be desirable to laminate filled film 10b to one or more substrates or support layers 30 such as is shown in FIG. 2. Lamination of the film may enhance the strength and thus durability of the film. If desired, filled film 10c may be attached to one or more support layers 30 to form a laminate 32. Referring again to FIG. 1, a conventional fibrous nonwoven web forming apparatus 48, such as a pair of spunbond machines, is used to form the support layer 30. The long, essentially continuous fibers 50 are deposited onto a forming wire 52 as an unbonded web 54 and the unbonded web 54 is then sent through a pair of bonding rolls 56 to bond the fibers together and increase the tear strength of the resultant web support layer 30. One or both of the rolls are often heated to aid in bonding. Typically, one of the rolls 56 is also patterned so as to impart a discrete bond pattern with a prescribed bond surface area to the web 30. The other roll is usually a smooth anvil roll but this roll also may be patterned if so desired. Once filled film 10b has been sufficiently stretched and the support layer 30 has been formed, the two layers are brought together and laminated to one another using a pair of laminating rolls or other means 58. As with the bonding rolls 56, the laminating rolls 58 may be heated. Also, at least one of the rolls may be patterned to create a discrete bond pattern with a prescribed bond surface area for the resultant laminate 32. Generally, the maximum bond point surface area for a given area of surface on one side of the laminate 32 will not exceed about 50 percent of the total surface area. There are a number of discrete bond patterns which may be used. See, for example, Brock et al., U.S. Pat. No. 4,041,203, which is incorporated herein by reference in its entirety. Once the laminate 32 exits the laminating rolls 58, it may be wound up into a roll 60 for subsequent processing. Alternatively, the laminate 32 may continue in-line for further processing or conversion.

While the support layers 30 and film 10b shown in FIG. 1 were bonded together through thermal point bonding, other bonding means can also be used. Suitable alternatives include, for example, adhesive bonding and the use of bond agents. In adhesive bonding, an adhesive such as a hot melt adhesive is applied between the film and fiber to bind the film and fiber together. The adhesive can be applied by, for example, melt spraying, printing or meltblowing. Various types of adhesives are available, including those produced from amorphous polyalphaolefins, ethylene vinyl acetate-based hot melts, and styrene block formulated adhesives available from Findley or National Standard. In addition, solvent-borne adhesives that are printed and cured on the film are also useful for bonding.

When the film and support layer(s) is bonded with a bond agent, the bond agent may be incorporated into the film itself. Suitable examples of bond agents include tackifiers, Catalloy® brand polymers, ethylene vinyl acetate and APAO. The bond agent essentially serves to increase adhesion between the film and fiber layers. For example, the film including a bond agent may be coextruded with the fiber support layer to form a laminate product without the use of adhesives. Alternatively, the film and fiber laminate may be thermally point-bonded, although generally very little heat is required since the bonding agent tends to increase the pressure sensitivity of the film and a bond somewhat like an adhesive bond can be formed.

The support layers 30 as shown in FIG. 2 are fibrous nonwoven webs. The manufacture of such fibrous nonwoven webs is known. Such fibrous nonwoven webs can add additional properties to filled film 10c such as a more soft, cloth-like feel. This is particularly advantageous when filled film 10c is being used as a barrier layer to liquids in such applications as outer covers for personal care absorbent articles and as barrier materials for hospital, surgical, and clean room applications such as, for example, surgical drapes, gowns and other forms of apparel. Attachment of the support layers 30 to the filled film 10c may be by the use of a separate adhesive such as hot-melt and solvent based adhesives or through the use of pressure (also known as thermal bonding) as with heated bonding rolls. When the filled film 10c includes metallocene-catalyzed elastomers, lamination is preferably achieved with adhesives.

The support layer in a laminate containing the film layer of the present invention can be necked polypropylene spunbond, crimped polypropylene spunbond, bonded carded webs, elastomeric spunbond or meltblown fabrics produced from elastomeric resins. A particularly advantageous support layer is a fibrous nonwoven web. Such webs may be formed from a number of processes including, but not limited to, spunbonding, meltblowing and bonded carded web processes. Meltblown fibers are formed by extruding molten thermoplastic material through a plurality of fine, usually circular, capillaries as molten threads or filaments into a high velocity usually heated gas stream such as air, which attenuates the filaments of molten thermoplastic material to reduce their diameters. Thereafter, the meltblown fibers are carried by the high velocity usually heated gas stream and are deposited on a collecting surface to form a web of randomly dispersed meltblown fibers. The meltblown process is well-known and is described in various patents and publications, including NRL Report 4364, "Manufacture of Super-Fine Organic Fibers" by B. A. Wendt, E. L. Boone and D. D. Fluharty; NRL Report 5265, "An Improved Device For The Formation of Super-Fine Thermoplastic Fibers" by K. D. Lawrence, R. T. Lukas, J. A. Young; U.S. Pat. No. 3,676,242, issued Jul. 11, 1972, to Prentice; and U.S. Pat. No. 3,849,241, issued Nov. 19, 1974, to Buntin, et al. The foregoing references are incorporated herein-by reference in their entirety.

Spunbond fibers are formed by extruding a molten thermoplastic material as filaments from a plurality of fine, usually circular, capillaries in a spinnerette with the diameter of the extruded filaments then being rapidly reduced, for example, by non-educative or educative fluid-drawing or other well-known spunbonding mechanisms. The production of spunbond nonwoven webs is illustrated in patents such as Appel et al., U.S. Pat. No. 4,340,563; Matsuki, et al., U.S. Pat. No. 3,802,817; Dorschner et al., U.S. Pat. No. 3,692,618; Kinney, U.S. Pat. Nos. 3,338,992 and 3,341,394; Levy, U.S. Pat. No. 3,276,944; Peterson, U.S. Pat. No. 3,502,538; Hartman, U.S. Pat. No. 3,502,763; Dobo et al., U.S. Pat. No. 3,542,615; and Harmon, Canadian Pat. No. 803,714. All of the foregoing references are incorporated herein by reference in their entirety.

A plurality of support layers 30 also may be used. Examples of such materials can include, for example, spunbond/meltblown laminates and spunbond/meltblown/spunbond laminates such as are taught in Brock et al., U.S. Pat. No. 4,041,203 which is incorporated herein by reference in its entirety.

Bonded carded webs are made from staple fibers which are usually purchased in bales. The bales are placed in a picker which separates the fibers. Next the fibers are sent through a combing or carding unit which further breaks apart and aligns the staple fibers in the machine direction so as to form a machine direction-oriented fibrous nonwoven web. Once the web has been formed, it is then bonded by one or more of several bonding methods. One bonding method is powder bonding wherein a powdered adhesive is distributed throughout the web and then activated, usually by heating the web and adhesive with hot air. Another bonding method is pattern bonding wherein heated calendar rolls or ultrasonic bonding equipment is used to bond the fibers together, usually in a localized bond pattern though the web can be bonded across its entire surface if so desired. When using the bicomponent staple fibers, through-air bonding equipment is, for many applications, especially advantageous.

The process shown in FIG. 1 also may be used to create a three-layer laminate. The only modification to the previously described process is to feed a supply 62 of a second fibrous nonwoven web support layer 30a into the laminating rolls 58 on a side of filled film 10b opposite that of the other fibrous nonwoven web support layer 30. As shown in FIG. 1, one or both of the support layers may be formed directly in-line, as is support layer 30. Alternatively, the supply of one or both support layers may be in the form of a preformed roll 62, as is support layer 30a. In either event, the second support layer 30a is fed into the laminating rolls 58 and is laminated to filled film 10b in the same fashion as the first support layer 30.

Figure 3:
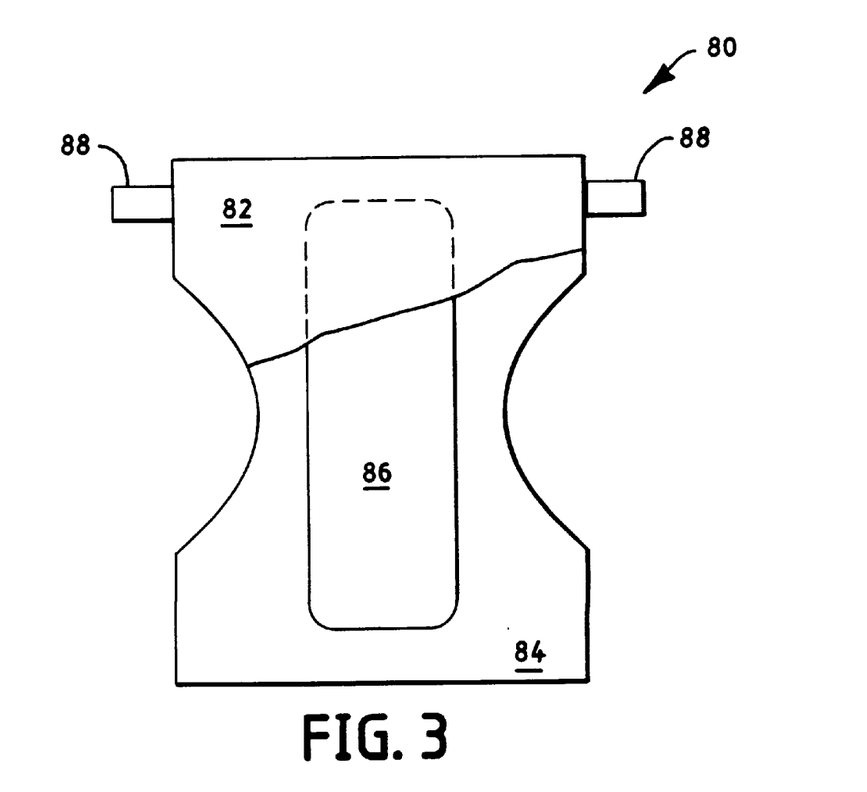
FIG. 3 is a partially cut away top plan view of an exemplary personal care absorbent article, in this case a diaper, which may utilize a laminate according to the present invention.

As has been stated previously, filled film 10b and the breathable laminate 32 may be used in a wide variety of applications not the least of which includes personal care absorbent articles such as diapers, training pants, incontinence devices and feminine hygiene products such as sanitary napkins. An exemplary article 80, in this case a diaper, is shown in FIG. 3 of the drawings. Referring to FIG. 3, most such personal care absorbent articles 80 include a liquid permeable top sheet or liner 82, a back sheet or outercover 84 and an absorbent core 86 disposed between and contained by the top sheet 82 and back sheet 84. Articles 80 such as diapers may also include some type of fastening means 88 such as adhesive fastening tapes or mechanical hook and loop type fasteners to maintain the garment in place on the weaver. The fastening system may contain stretch material to form "stretch ears" for greater comfort.

Filled film 10b by itself or in other forms such as the film 10c/support layer 30 laminate 32 may be used to form various portions of the article including, but not limited to, stretch region, the top and the back sheet 84. If the film or laminate is to be used as the liner 82, it will most likely-have to be apertured or otherwise made to be liquid permeable. When using a film/nonwoven laminate as the outercover 84, it is usually advantageous to place the nonwoven side facing out away from the user. In addition, in such embodiments it may be possible to utilize the nonwoven portion of the laminate as the loop portion of the hook and loop combination.

Other uses for the filled film and breathable film/support layer laminates according to the present invention include, but are not limited to, automobile and boat covers that protect the vehicle from sand, from damage, weather elements, surgical drapes and gowns, wipers, barrier materials and articles of clothing or portions thereof including such items as workwear and lab coats.

The advantages and other characteristics of the present invention are best illustrated by the following examples:

EXAMPLE 1

Two film samples having the composition listed in Table I below were extruded. Each sample was about 1.5 millimeters thick (about 54 g/square meter basis weight), and was stretched under the stretch conditions detailed below.

The water vapor transmission rates of the stretched films were measured in accordance to the WVTR method detailed below. The composition of each sample film and the result of this analysis are listed in Table I.

Stretch Conditions

The samples were stretched on a machine-direction-orienter (MDO), preheat rolls 140° F., slow niproll 60°F., fast niproll 57°F., first annealing roll 55° F., second annealing roll 107° F. The MDO out-speed was 184 fpm, winder speed was 157 fpm, and the infeed speed was varied to get a desired stretch (roll-speed) ratio.

Water Vapor Transmission Data

The water vapor transmission rate (WVTR) for the sample materials was calculated in accordance with ASTM Standard E96-80. Circular samples measuring three inches in diameter were cut from each of the test materials and a control which was a piece of CELGARD® 2500 film from Hoechst Celanese Corporation of Sommerville, New Jersey. CELGARD® 2500 film is a microporous polypropylene film. Three samples were prepared for each material. The test dish was a number 60-1 Vapometer pan distributed by Thwing-Albert Instrument Company of Philadelphia, Pa. One hundred milliliters of water were poured into each Vapometer pan and individual samples of the test materials and control material were placed across the open tops of the individual pans. Screw-on flanges were tightened to form a seal along the edges of the pan, leaving the associated test material or control material exposed to the ambient atmosphere over a 6.5 centimeter diameter circle having an exposed area of approximately 33.17 square centimeters. The pans were placed in a forced air oven at 100° F. (32° C.) for 1 hour to equilibrate. The oven was a constant temperature oven with external air circulating through it to prevent water vapor accumulation inside. A suitable forced air oven is, for example, a Blue M Power-O-Matic 60 oven distributed by Blue M Electric Company of Blue Island, Ill. Upon completion of the equilibration, the pans were removed from the oven, weighed and immediately returned to the oven. After 24 hours, the pans were removed from the oven and weighed again. The preliminary test water vapor transmission rate values were calculated with Equation (I) below:

Test WVTR=(grams weight loss over 24 hours)×315.5 g/m$^2$/24hr(I)

The relative humidity within the oven was not specifically controlled.

Under predetermined set conditions of 100° F. (32° C.) and ambient relative humidity, the WVTR for the CELGARD® 2500 control has been defined to be 5000 grams per square meter for 24 hours. Accordingly, the control sample was run with each test and the preliminary test values were corrected to set conditions using equation II below:

WVTR=(Test WVTR/control WVTR)×(5000 g/m$^2$/24hrs)  (II)

TABLE I

| Film Sample | Composition of Sample | | Stretch Ratio | WVTR g/m$^2$-24 hrs) | Stretched Basis Weight (g/m$^2$) | Percent Set |
|---|---|---|---|---|---|---|
| | Filler (amount in filled film) | Polymeric Resin | | | | |
| 1 | CaCO$_3$ (55 wt %) | Catalloy ® KS-057P | 3.5 | 1,844 | 21 | 39% |
| 2 | CaCO$_3$ (55 wt %) | Catalloy ® KS-057P | 3.75 | 2,069 | 17 | 39% |
| 3 | CaCO$_3$ (60 wt %) | Vector ® 4411 | 5 | 2,000 | 84 | 60% |

[1] Ratio of speed between slow and fast nirolls.

As shown above, the sample made from Vector 4411 had a high basis weight but nevertheless exhibited desirable WVTR. The basis weight can be lowered further by increasing the film extrusion temperature or adding a viscosity reducing agent to the filled polymer. The two film samples made from Catalloy exhibited desirable WVTR's, at lower basis weights.

EXAMPLE 2

For Example 2 and Comparative Examples 1 and 2, the test procedures described below were used to evaluate the films and laminate.

Cycle Test

A 3" wide by 6" long strip of the sample material was pulled to an elongated length of 160% and 200% of the original grip distance of 3 inches. The sample is elongated at a rate of 20 in/min for two cycles. Upon return after the second cycle, the elongation at which no load is first detected is recorded. This value is used as the final length in the immediate recovery calculation below.

$$\text{Immediate Recovery} = \frac{\text{Maximum Length} - \text{Final Length}}{\text{Maximum Length} - \text{Initial Length}} \times 100\% \quad (I)$$

The sample is then held at zero elongation for one minute. At this time, the sample is elongated until a load is detected. This value is used as the final length to calculate delayed recovery.

$$\text{Delayed Recovery} = \frac{\text{Maximum Length} - \text{Final Length}}{\text{Maximum Length} - \text{Initial Length}} \times 100\% \quad (II)$$

Hysteresis Loss

A 3 inch wide by 6 inch long strip of each sample is stretched to 160% of its unbiased length. The stretching apparatus was SINTECH Model 1/5 or Model 2/5 from Syntech Division of MTS Systems Corp., Research Triangle Park, N.C. 27709-4226. This cycle of 60% elongation was repeated two times. The % hysteresis loss was calculated in accordance to Equation III below.

$$\text{Hysteresis} = 100\% \left( \frac{\text{area under loading stress/strain curve} - \text{area under unloading stress strain curve}}{\text{area under loading curve}} \right) \quad (III)$$

Tensile Test

A 3" wide by 6" long strip of each sample was elongated at a rate of 20 in/min until it broke. Peak load and elongation at peak load were acquired. The results are shown in Table II below.

Permanent Elongation

An evaluation was performed to determine the amount of permanent elongation of the film and comparative materials.

A 3 inch wide by 6 inch long strip of each sample was stretched with the Syntech equipment described above. Each strip was stretched to 160% the unbiased length and held at the stretched length for one minute. The zero load extension value, which is the distance that the jaws of the tensile test equipment move at the beginning of the second cycle before a load is registered by the equipment, was obtained from the tensile test equipment. The zero load extension value was then used to calculate % set with Equation IV below.

$$\% \text{ set} = \frac{\text{zero load extension after one cycle}}{\text{initial sample gauge length}} \times 100\% \quad (IV)$$

After the second cycle, the sample was held at 60% elongation for one minute. The sample is then returned to zero elongation. Upon this return, the length at which no load is initially detected is used as the final length for the Immediate Set calculation below:

$$\text{Immediate Set} = \frac{\text{Final Length} - \text{Initial Length}}{\text{Final Length}} \quad (V)$$

The sample is then held at zero elongation for one minute. At that time the sample is elongated until a load is detected. The length at which this load is detected is used to calculate Delayed Set:

$$\text{Delayed Set} = \frac{\text{Final Length} - \text{Initial Length}}{\text{Final Length}} \quad (VI)$$

Recovery is defined as the difference between immediate set and delayed set. No recovery indicates that the two values were identical. A blown film of the composition (% by weight) listed in Table II below was extruded:

TABLE II

55% Supercoat ™ calcium carbonate, average particle size of 1 micron, available from English China Clay Company of America, Sylacauga, AL;
45% Affinity ™ 8200 resin (0.870 g/cc, 5 MI), an (ethylene 1-octene) copolymer made with a single-site catalyst, available from Dow Chemical Co. of Midland, MI; and
600 ± ppm of an antioxidant package.

The 20-inch wide 1.5 mils thick film was then stretch-oriented in the machine direction (MD) at a stretch ratio of 5.4× (fast niproll speed divided by the slow nip speed), all rolls being at room temperature (65–70° F.). Film inlet speed was 30 fpm, outlet speed 162 fpm on the MDO, and the stretched film was wound up at about 98 fpm so that the film could be wound up under the lowest tension. This gives an effective stretch ratio of 3.25× from film inlet to the MDO to the winder. The film was completely whitened indicating porosity, with a measured WVTR of 1618 $g/m^2/day$. The film displayed very good elastic behavior in both the CD and MD direction.

The film so made was tested for its elastic behavior using tests described above. Testing the samples in the cross direction (CD), that is, perpendicular to the direction of orientation, average of four specimens tested, the values obtained are listed in Table III below:

TABLE III

| Property | at 60% Elongation | at 100% Elongation |
|---|---|---|
| Immediate Recovery | 71.31% | 63.92% |
| Immediate Set | 17.22% | 36.08% |
| Delayed Recovery | 85.27% | 80.59% |
| Delayed Set | 08.84% | 19.41% |
| First Cycle Hysteresis Loss | 59.70% | 67.90% |
| 2$^{nd}$ Cycle Hysteresis Loss | 39.00% | 44.60% |

TABLE III-continued

| Property | at 60% Elongation | at 100% Elongation |
|---|---|---|
| Peak (Breaking) Tensile Load | | 334.0 grams |
| Peak (Breaking) Elongation | | 660.4% |

Comparative Example 1

A commercially available breathable film, EXXAIRE™ XBF-511W, available from Exxon Chemical Company of Houston, Tex. was also tested using the same test procedures. This film, essentially inelastic, has an undisclosed amount of filler, it is a uniaxially oriented microporous LLDPE film with WVTR of 3840 g/m²/day as measured by the test procedure described above. Cycle testing was done perpendicular to the direction of orientation. The values obtained are listed in Table IV below.

TABLE IV

| Property | at 60% Elongation |
|---|---|
| Immediate Recovery | 39.9% |
| Delayed Recovery | 73.5% |
| First Cycle Hysteresis Loss | 86.7% |
| 2nd Cycle Hyesteresis Loss | 67.9% |
| Peak (Breaking) Tensile Load | 975 grams |
| Peak (Breaking) Elongation | 245% |

Comparative Example 2

A cast film of the following composition (% by weight) was extruded:

60% Supercoat™ calcium carbonate, as in

EXAMPLE 2

40% Exceed® 357C80, a metallocene-catalyzed (ethylene 1-butene) copolymer (0.917 g/cc, 3.4 MI), available from Exxon Chemical Co. of Houston, Tex. and 1000±ppm of an antioxidant package.

The extruded 1.5-mil thick film was then stretch-oriented in the machine direction at a stretch ratio of 4×. The preheat rolls and slow and fast niprolls were set at 170° F., and the annealing roll at 200° F. Film inlet speed was 100 fpm, and the stretched film was wound up at about 400 fpm. The film was completely whitened, and the measured WVTR was 4590 g/m²/day. This film was also tested perpendicular to the direction of orientation with the following values obtained. The values obtained are listed in Table V below.

TABLE V

| Property | at 60% Elongation |
|---|---|
| Immediate Recovery | 51.6% |
| Delayed Recovery | 70.4% |
| First Cycle Hysteresis Loss | 79.25% |
| 2nd Cycle Hyesteresis Loss | 57.4% |
| Peak (Breaking) Tensile Load | 394 grams |

TABLE V-continued

| Property | at 60% Elongation |
|---|---|
| Peak (Breaking) Elongation | 269% |

Although this film is made with a metallocene-type of copolymer, it is essentially inelastic because of the higher density of the copolymer.

EXAMPLE 3

A blown film of the following composition (% by weight) was extruded:

55% Supercoat™ calcium carbonate, average particle size of 1 micron, available from English China Clay Company of America, Sylacauga, Ala., 45% Affinity™ 8200 resin (0.870 g/cc, 5 MI), an (ethylene 1-octene) copolymer made with a single-site catalyst, available from Dow Chemical Co. of Midland, Mich., and 600± ppm of an antioxidant package.

The 20-inch wide 1.5 mils thick film was then stretch-oriented in the machine direction (MD) on equipment commonly known in the art as MDO, at a stretch ratio of 5.0× (fast niproll speed divided by the slow niproll speed), all rolls being at room temperature (about 70° F.), except the last roll which was set at 120° F. to anneal the film. Film inlet speed was 60 fpm, outlet speed from the MDO was 300 fpm, and the film was then directed to a winder whose speed was adjusted to allow the film to relax but without any slack or sag before the winder. A sheet of necked spunbond (previously stretched to neck to 40% of its original width, ending basis weight of 0.9 ounce per square yard) was then unwound, directed under a spray-head, which was positioned between the MDO and the winder, where the spunbond was sprayed with a molten hotmelt (Rextac™ RT-2330, available from Rexene Corp. of Odessa, Tex.) at adhesive add-on level of 3 grams/m², the so-sprayed spunbond was then directed to niprolls just before the winder where the film and the spunbond were contacted to consummate the lamination, and the laminate was wound up at a speed of 155 fpm. The laminate so made had a smooth, cloth-like appearance on one side, it was soft and elastic (extensible with snap-back) in the CD-direction withstanding repeated stretching without delamination. The laminate was breathable with WVTR measured at 1374 g/m²/day.

The laminate so made was tested for its elastic behavior using tests described above Testing the sample in the cross direction (CD), that is, in the direction of its extensibility and perpendicular to the direction of film orientation, average of four specimens tested, the values obtained are listed in Table VI below:

TABLE VI

| Property | at 60% elongation | at 100% elongation |
|---|---|---|
| immediate recovery | 70.73% | 66.50% |
| immediate set | 17.56% | 33.50% |
| delayed recovery | 85.64% | 82.87% |

TABLE VI-continued

| Property | at 60% elongation | at 100% elongation |
|---|---|---|
| first cycle hysteresis | 68.2% | 76.6% |
| 2$^{nd}$ cycle hysteresis | 42.0% | 48.2% | peak (breaking) tensile load 2,326.4 grams
peak (breaking) elongation 221.7%

Therefore, the films of the present invention have high water vapor transmission rate and elasticity that impart a wide variety of functionalities including vapor permeability, liquid impermeability, and comfort fit and stretch. Furthermore, such films can be attached to support layers to form laminates.

Of course, it should be understood that a wide range of changes and modifications can be made to the embodiments described above. It is therefore intended that the foregoing description illustrates rather than limits this invention, and that it is the following claims, including all equivalents, which define this invention.

We claim:

1. A breathable film comprising:

An oriented microporous relaxed unbiased film layer (10c) comprising an elastomeric polymer resin and at least 30% by weight of a filler having a particle size that contributes to pore formation, the relaxed unbiased film layer formed from an unstretched filled film (10a) having an original length a stretched length (10b), said relaxed unbiased film layer including a permanent elongation of at least about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, wherein said elastomeric polymer includes at least one of a) ethylene-propylene elastomer blends, b) ethylene copolymers, c) block copolymers including styrene, d) terpolymers of ethylene and propylene, e) molecular blends of at least two polymers of propylenes or polymers of propylene with ethylene, f) ethylene vinyl acetate, g) ethylene-normal butyl acrylate, or h) ethylene methyl acrylate.

2. The film of claim 1 wherein said film layer has a water vapor transmission rate of from about 1,000 g/m$^2$/24 hrs to about 4,500 g/m$^2$-24 hrs.

3. The film of claim 1 wherein said polymer comprises ethylene-vinyl acetate including about 26% acetate.

4. The film of claim 1 wherein said polymer comprises ethylene-normal butyl acrylate including about 20% acrylate.

5. The film of claim 1 wherein said polymer comprises ethylene methyl acrylate including about 20% acrylate.

6. The film of claim 1 wherein said film layer has a water vapor transmission rate above 4,500 g/m$^2$/24 hrs.

7. A process for forming a breathable elastic film capable of being elongated to a stretched length at least one and a half times its starting length and recovering at least half of its elongation, the process comprising:

a) providing an unstretched filled film layer comprising at least 30% by weight of a filler having a particle size that contributes to pore formation and an elastomeric polymeric material having a first length, b) stretching said filled film layer to a second length that is at least about two times said first length so as to create a stretched filled microporous film layer, c) relaxing said stretched filled microporous film layer of step b so as to produce a film with a permanent elongation of at least one and a half times said first length.

8. The process of claim 7 wherein said second length is from about two times to about six times said first length.

9. The process of claim 7 wherein said second length is from about three times to about four times said first length.

10. The process of claim 7 wherein said second length is from about five times to about six times said first length.

11. The process of claim 7 wherein said stretched filled microporous film layer has a water vapor transmission rate of at least about 1,000 g/m$^2$-24 hrs.

12. The process of claim 8 wherein said stretched filled microporous film layer has a water vapor transmission rate of at least about 4,500 g/m$^2$/24 hrs.

13. The process of claim 7 where in step c said stretched filled microporous film layer of step b is relaxed so as to produce a film with a permanent elongation of about 3 times said first length.

14. A breathable film comprising:

an oriented microporous relaxed unbiased film layer (10c) including an elastomeric polymer resin and at least 30% by weight of a filler having a particle size that contributes to pore formation and coated with a fatty acid, the relaxed unbiased film layer formed from an unstretched filled film (10a) having an original length a stretched length (10b), said relaxed unbiased film layer including a permanent elongation of at least about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, and wherein said elastomeric polymer includes at least one of a) ethylene-propylene elastomer blends, b) ethylene copolymers, c) block copolymers including styrene, d) terpolymers of ethylene and propylene, e) molecular blends of at least two polymers of propylenes or polymers of propylene with ethylene, f) ethylene vinyl acetate, g) ethylene-normal butyl acrylate, or h) ethylene methyl acrylate.

15. A breathable film comprising:

An oriented microporous relaxed unbiased film layer (10c) comprising an elastomeric polymer resin and at least 30% by weight of a filler having a particle size that contributes to pore formation and coated with a fatty acid, the relaxed unbiased film layer formed from an unstretched filled film (10a) having an original length a stretched length (10b), said relaxed unbiased film layer including a permanent elongation of about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, and wherein said elastomeric polymer includes at least one of a) ethylene-propylene elastomer blends, b) ethylene copolymers, c) block copolymers including styrene, d) terpolymers of ethylene and propylene, e) molecular blends of at least two polymers of propylenes or polymers of propylene with ethylene, f) ethylene vinyl acetate, g) ethylene-normal butyl acrylate, or h) ethylene methyl acrylate.

16. A breathable film comprising:

An oriented microporous relaxed unbiased film layer (10c) comprising an elastomeric polymer resin and at least 30% by weight of a filler having a particle size that contributes to pore formation, the relaxed unbiased film layer formed from an unstretched filled film (10a) having an original length a stretched length (10b), said relaxed unbiased film layer including a permanent elongation of about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, wherein said elastomeric polymer includes at least one of a) ethylene-propylene elastomer blends, b) ethylene copolymers, c) block copolymers including styrene, d) terpolymers of ethylene and propylene, e) molecular blends of at least two polymers of propylenes or polymers of propylene with ethylene, f) ethylene vinyl acetate, g) ethylene-normal butyl acrylate, or h) ethylene methyl acrylate.

17. A breathable film comprising:

An oriented microporous relaxed unbiased film layer (10c) comprising an elastomeric polymer resin and at least 30% by weight of a filler having a particle size that contributes to pore formation, the relaxed unbiased film layer formed from an unstretched filled film (10a) having an original length a stretched length (10b), said relaxed unbiased film layer including a permanent elongation of at least about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, wherein said elastomeric polymer comprises a block copolymer including styrene and at least one of ethylene, butylene and isoprene.

18. A breathable film comprising:

An oriented microporous relaxed unbiased film layer (10c) comprising an elastomeric polymer resin and at least 30% by weight of a filler having a particle size that contributes to pore formation, the relaxed unbiased film layer formed from an unstretched filled film (10a) having an original length a stretched length (10b), said relaxed unbiased film layer including a permanent elongation of at least about 1.5 times the original length, and said relaxed unbiased film layer (10c) capable of having a room-temperature biased length that is at least about one and a half times said relaxed unbiased film layer length and a release length, upon release of a biasing force of no more than one and one quarter of the relaxed unbiased film layer length, having a water vapor transmission rate of at least about 1,000 g/m$^2$-24 hrs, wherein said elastomeric polymer includes a metallocene-catalyzed elastomer.

* * * * *